(12) United States Patent
Rakshit et al.

(10) Patent No.: US 12,738,359 B2
(45) Date of Patent: Sep. 15, 2026

(54) FIRST AID TREATMENT FOR WORKERS USING DETACHABLE ROBOTS ON ROBOTIC SUIT

(71) Applicant: INTERNATIONAL BUSINESS MACHINES CORPORATION, Armonk, NY (US)

(72) Inventors: Sarbajit K. Rakshit, Kolkata (IN); Shilpa Shetty, Sydney (AU); Sathya Santhar, Ramapuram (IN); Sridevi Kannan, Chennai (IN)

(73) Assignee: International Business Machines Corporation, Armonk, NY (US)

( * ) Notice: Subject to any disclaimer, the term of this patent is extended or adjusted under 35 U.S.C. 154(b) by 213 days.

(21) Appl. No.: 18/493,260

(22) Filed: Oct. 24, 2023

(65) Prior Publication Data

US 2025/0132010 A1 Apr. 24, 2025

(51) Int. Cl.
*G16H 20/40* (2018.01)

(52) U.S. Cl.
CPC .................................. *G16H 20/40* (2018.01)

(58) Field of Classification Search
CPC ...................................................... G16H 20/40
See application file for complete search history.

(56) References Cited

U.S. PATENT DOCUMENTS

2018/0092536 A1 4/2018 Sandler
2019/0224841 A1 7/2019 Ly
2019/0374161 A1 12/2019 Ly
2021/0034837 A1* 2/2021 Kim .................... A01K 27/002
2022/0079792 A1* 3/2022 Lear ........................ A61B 5/11

FOREIGN PATENT DOCUMENTS

CN 210161170 U * 3/2020
CN 112589811 A * 4/2021 ............ B25J 9/1679
CN 114536407 A * 5/2022 ............ A61G 12/00
(Continued)

OTHER PUBLICATIONS

These Robots Come to the Rescue after a Disaster | Robin Murphy | TED Talks | https://www.youtube.com/watch?v=wG4RnDNWtJo (Year: 2015).*

(Continued)

*Primary Examiner* — Ramon A. Mercado
*Assistant Examiner* — John Martin O'Malley
(74) *Attorney, Agent, or Firm* — Jordan T. Schiller

(57) ABSTRACT

A method for robotically providing first aid treatment to an affected worker, wherein the affected worker is wearing a robotic suit that further comprises an exoskeleton and one or more secondary detachable robots. The method includes receiving biometric and visual parameters of the affected worker and identifying, by the one or more secondary detachable robots, a context and type of injury to the affected worker. The method further includes determining a first aid treatment plan for the affected worker, based on the identified context and type of injury. The method further includes activating the one or more secondary detachable robots on the robotic suit, based on the determined first aid treatment plan and providing the determined first aid treatment plan to the affected worker, by the activated one or more secondary detachable robots.

20 Claims, 3 Drawing Sheets

(56) References Cited

FOREIGN PATENT DOCUMENTS

| | | | | | |
|---|---|---|---|---|---|
| CN | 217394950 U | * | 9/2022 | | |
| CN | 116665115 A | * | 8/2023 | ............. | G16H 50/20 |

OTHER PUBLICATIONS

CTRL Robotics, "It's time to take control of your hospital and make it better.", accessed on Jul. 18, 2023, 3 pages, https://ctrlrobotics.com/hospital-robot-interest-form/.

Ford Media Center, "Ford Rolls Out Exoskeleton Wearable Technology Globally to Help Lessen Worker Fatigue, Injury", Aug. 7, 2018, 2 pages, https://media.ford.com/content/fordmedia/fna/us/en/news/2018/08/07/ford-rolls-out-exoskeleton-wearable-technology-globally-to-help-.html.

Hodson, "Robotic suit gives shipyard workers super strength", New Scientist, Jul. 30, 2014, 7 pages, https://www.newscientist.com/article/mg22329803-900-robotic-suit-gives-shipyard-workers-super-strength/.

* cited by examiner

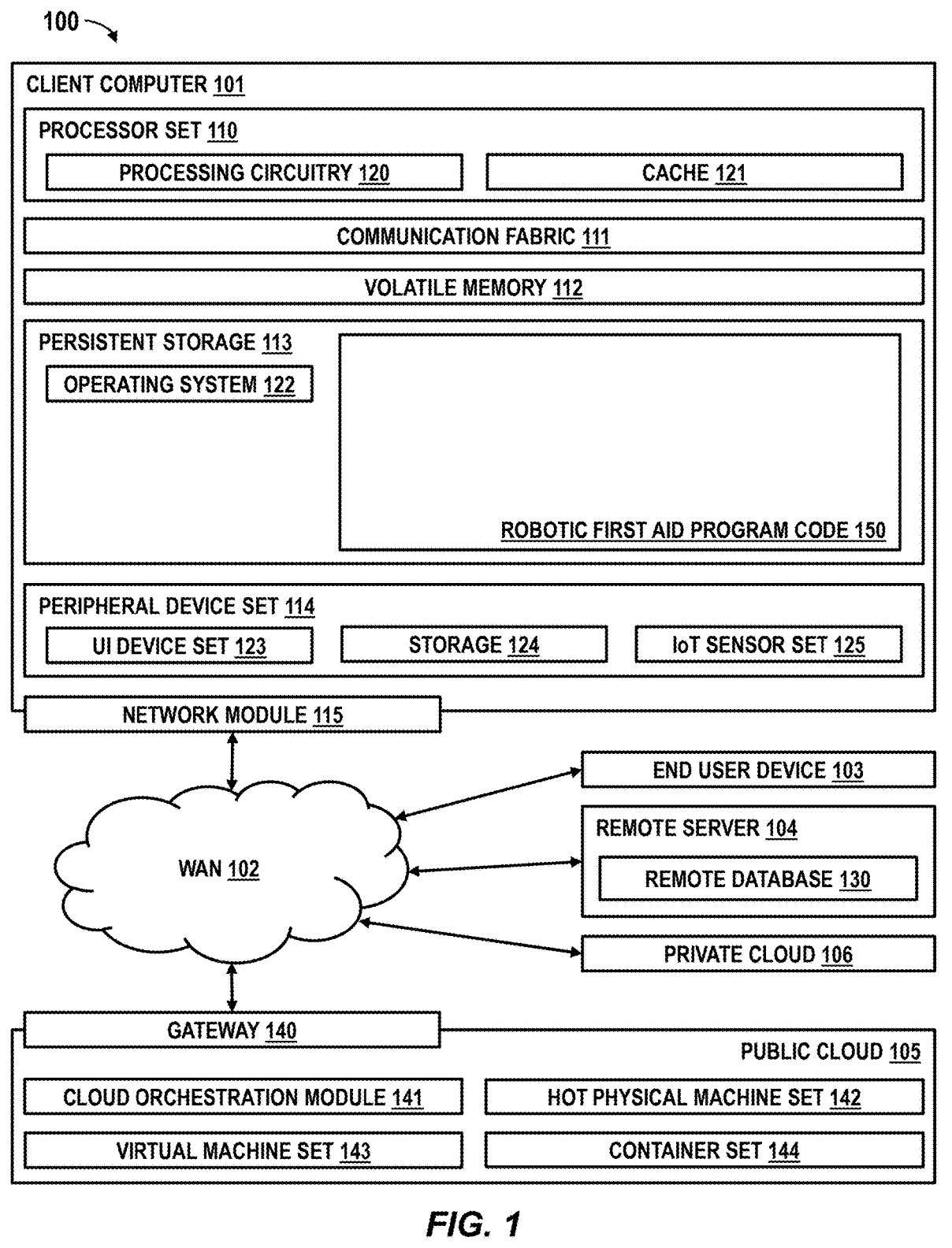

100

CLIENT COMPUTER 101
PROCESSOR SET 110
PROCESSING CIRCUITRY 120
CACHE 121
COMMUNICATION FABRIC 111
VOLATILE MEMORY 112
PERSISTENT STORAGE 113
OPERATING SYSTEM 122
ROBOTIC FIRST AID PROGRAM CODE 150
PERIPHERAL DEVICE SET 114
UI DEVICE SET 123
STORAGE 124
IoT SENSOR SET 125
NETWORK MODULE 115
END USER DEVICE 103
WAN 102
REMOTE SERVER 104
REMOTE DATABASE 130
PRIVATE CLOUD 106
GATEWAY 140
PUBLIC CLOUD 105
CLOUD ORCHESTRATION MODULE 141
HOT PHYSICAL MACHINE SET 142
VIRTUAL MACHINE SET 143
CONTAINER SET 144

*FIG. 1*

FIRST AID TREATMENT FOR WORKERS USING DETACHABLE ROBOTS ON ROBOTIC SUIT

BACKGROUND

The present disclosure relates generally to the field of cognitive computing, robotics, and more particularly to dynamic first aid treatment, via robotic technology, based on contextual events.

In industries such as shipbuilding, automobile manufacturing, mining, and others where workers are in confined spaces or lifting heavy materials, workplace safety is becoming increasingly important. For example, various automobile companies have introduced wearable exoskeleton robots so that their workers are more effective, and face less fatigue, on the industrial floor. In the shipbuilding industry, workers building the world's biggest ships may soon be wearing exoskeletons that give them superhuman strength to haul 100-kilogram hunks of metal as if they're nothing.

Typically, when there is an accident to industrial workers, first aid is provided by other human workers. However, when workers are performing an activity alone (e.g., mining, hauling heavy equipment, etc.) there may not be any co-workers nearby to quickly assist the injured worker.

BRIEF SUMMARY

Embodiments of the present invention disclose a method, a computer program product, and a system.

According to an embodiment, a method, in a data processing system including a processor and a memory, for robotically providing first aid treatment to an affected worker, wherein the affected worker is wearing a robotic suit that further comprises an exoskeleton and one or more secondary detachable robots. The method includes receiving biometric and visual parameters of the affected worker and identifying, by the one or more secondary detachable robots, a context and type of injury to the affected worker. The method further includes determining a first aid treatment plan for the affected worker, based on the identified context and type of injury. The method further includes activating the one or more secondary detachable robots on the robotic suit, based on the determined first aid treatment plan and providing the determined first aid treatment plan to the affected worker, by the activated one or more secondary detachable robots.

A computer program product, according to an embodiment of the invention, includes a non-transitory tangible storage device having program code embodied therewith. The program code is executable by a processor of a computer to perform a method. The method includes receiving biometric and visual parameters of the affected worker and identifying, by the one or more secondary detachable robots, a context and type of injury to the affected worker. The method further includes determining a first aid treatment plan for the affected worker, based on the identified context and type of injury. The method further includes activating the one or more secondary detachable robots on the robotic suit, based on the determined first aid treatment plan and providing the determined first aid treatment plan to the affected worker, by the activated one or more secondary detachable robots.

A computer system, according to an embodiment of the invention, includes one or more computer devices each having one or more processors and one or more tangible storage devices; and a program embodied on at least one of the one or more storage devices, the program having a plurality of program instructions for execution by the one or more processors. The program instructions implement a method. The method includes receiving biometric and visual parameters of the affected worker and identifying, by the one or more secondary detachable robots, a context and type of injury to the affected worker. The method further includes determining a first aid treatment plan for the affected worker, based on the identified context and type of injury. The method further includes activating the one or more secondary detachable robots on the robotic suit, based on the determined first aid treatment plan and providing the determined first aid treatment plan to the affected worker, by the activated one or more secondary detachable robots.

BRIEF DESCRIPTION OF THE DRAWINGS

FIG. 1 depicts a diagram graphically illustrating the hardware components of a computing environment 100, such as robotic first aid computing environment 200, and a cloud computing environment, in accordance with an embodiment of the present invention.

DETAILED DESCRIPTION

Figure 2:
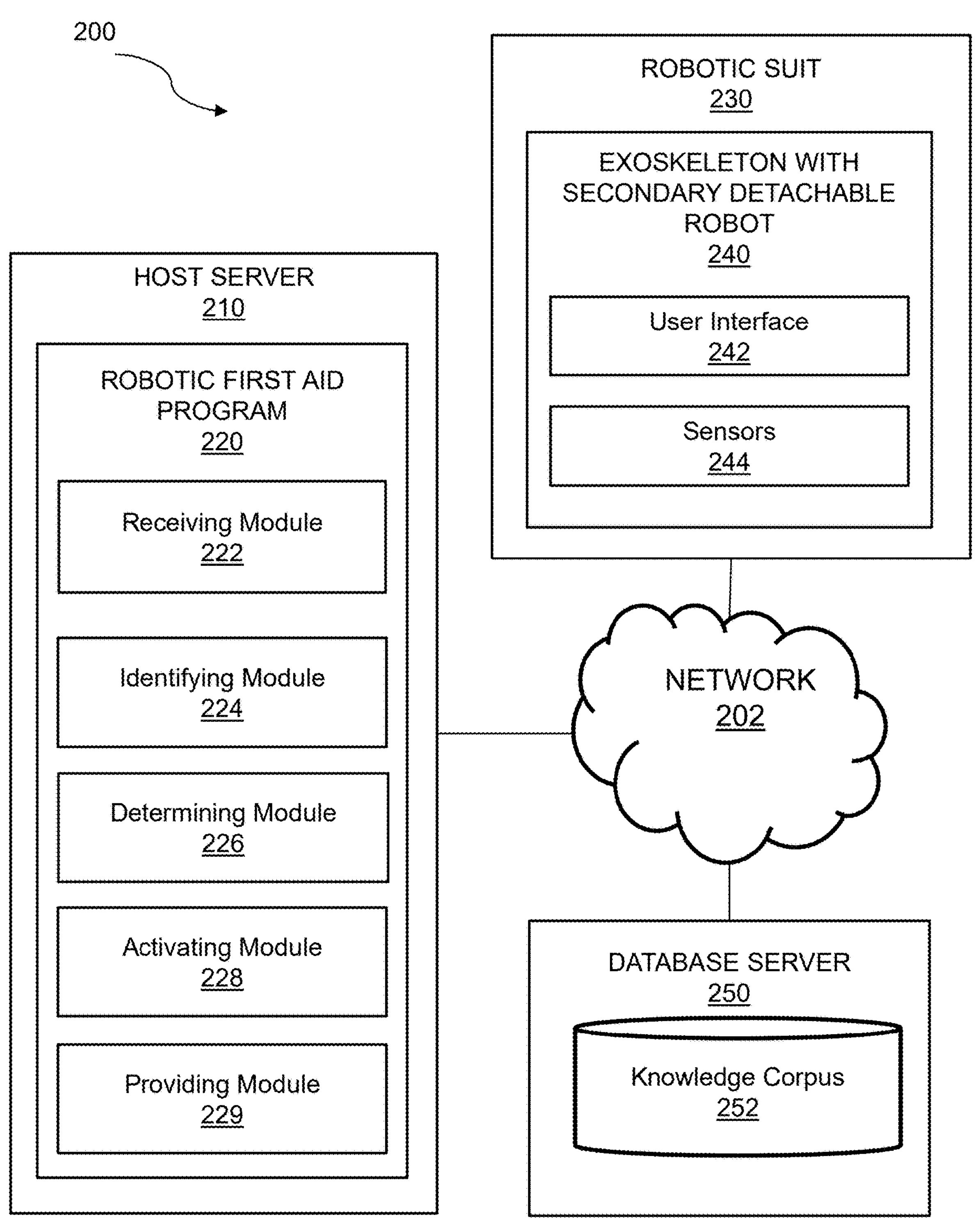
FIG. 2 illustrates robotic first aid computing environment 200, in accordance with an embodiment of the present invention.

In various type of work environments, workers are hauling heavy materials (e.g., shipyards, construction sites, automobile factories, and so forth) or are engaged in confined areas (e.g., mining shafts, remote rescue operations, etc.). In these scenarios, an injured worker may need immediate first aid treatment with no help in sight.

Nowadays, various automobile companies have introduced a wearable exoskeleton robotic suit in their industrial activities to make human workers more effective on the industrial floor, and less prone to fatigue and injury. Employees are thus able to use the wearable exoskeleton to help lessen the physical toll that their job takes on their body. For example, the wearable exoskeleton elevates and supports a worker's arms while performing overhead tasks such as reaching up with a power tool to screw bolts to secure a car's brace, all while standing underneath the vehicle.

Workers that are wearing exoskeleton robotic suits could be performing activities in areas such as rescue operations or mine shafts, where there is limited space, and the worker needs to operate individually. If the worker is injured or faces a threat from the surrounding area, the worker needs to have the ability to provide an appropriate level of protection or have a proactive alert to co-workers about the difficult situation.

Additionally, if the worker is injured on the job with no co-workers nearby, the worker needs to receive appropriate first aid treatment, at least until a rescue team can arrive and administer additional medical care.

Currently, there is no autonomous robotic first aid treatments available to injured workers.

The present invention discloses a solution that performs a first aid treatment to an injured worker via the exoskeleton robotic suit and invention module (i.e., robotic first aid program 220).

Hereinafter, exemplary embodiments of the present invention will be described in detail with reference to the attached drawings.

The present invention is not limited to the exemplary embodiments below, but may be implemented with various modifications within the scope of the present invention. In addition, the drawings used herein are for purposes of illustration, and may not show actual dimensions.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation, or garbage collection, but this does not render the storage device as transitory because the data is not transitory while it is stored.

FIG. 1 depicts a diagram graphically illustrating the hardware components of a computing environment 100, such as robotic first aid computing environment 200, and a cloud computing environment in accordance with an embodiment of the present invention.

Computing environment 100 contains an example of an environment for the execution of at least some of the computer code involved in performing the inventive methods, such as robotic first aid program code 150. In addition to the robotic first aid program code 150, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and robotic first aid program code 150, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in robotic first aid program code 150 in persistent storage 113.

COMMUNICATION FABRIC 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid-state storage devices. Operating system 122 may take several forms, such as various known proprietary operating systems or open-source Portable Operating System Interface type operating systems that employ a kernel. The code included in robotic first aid program code 150 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101) and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

FIG. 2 illustrates robotic first aid computing environment 200, in accordance with an embodiment of the present invention. Robotic first aid computing environment 200 includes host server 210, robotic suit 230, and database server 250, all connected via network 202. The setup in FIG. 2 represents an example embodiment configuration for the present invention and is not limited to the depicted setup to derive benefit from the present invention.

In an exemplary embodiment, host server 210 includes robotic first aid program 220. In various embodiments, host server 210 may be a laptop computer, tablet computer, netbook computer, personal computer (PC), a desktop computer, a personal digital assistant (PDA), a smart phone, or any programmable electronic device capable of communicating with robotic suit 230, and database server 250, via network 202. Host server 210 may include internal and external hardware components, as depicted, and described in further detail with reference to FIG. 1. In other embodiments, host server 210 may be implemented in a cloud computing environment, as further described in relation to FIG. 1. Host server 210 may also have wireless connectivity capabilities allowing it to communicate with robotic suit 230, database server 250, and other computers or servers over network 202.

With continued reference to FIG. 2, robotic suit 230 includes secondary detachable robot 240. In various embodiments, robotic suit 230 may be a wearable device or any programmable electronic device capable of communicating with host server 210, secondary detachable robot 240, and database server 250, via network 202. Robotic suit 230 may include internal and external hardware components, as depicted, and described in further detail with reference to FIG. 1. In other embodiments, robotic suit 230 may be implemented in a cloud computing environment, as described in relation to FIG. 1. Robotic suit 230 may also have wireless connectivity capabilities allowing it to communicate with host server 210, database server 250, and other computers or servers over network 202.

In exemplary embodiments, robotic suit 230 is a powered exoskeleton (e.g., a mobile machine) which is wearable over all or part of the human body, providing ergonomic structural support and powered by a system of electric motors, pneumatics, levers, hydraulics, or a combination of cybernetic technologies, while allowing for sufficient limb movement with increased strength and endurance.

In exemplary embodiments, robotic suit 230 is equipped with a first aid kit. The first aid kit may contain various types of tools, technologies, and medical equipment that are suitable to the type of landscape and working environment the worker is in. For example, in a rescue mission deep in the Amazon jungle, the first aid kit may include tourniquets and a treatment for snake bites. Alternatively, if the worker is in a mine shaft, the first aid kit may further include an easy fold stretcher and inflatable leg splints.

In further exemplary embodiments, robotic first aid program 220 equips the first aid kit attached to the robotic suit 230 based on historically identified types of injuries (e.g., identified from knowledge corpus 252) in a particular activity area.

In exemplary embodiments, the robotic suit 230 is designed to provide better mechanical load tolerance, and its control system aims to sense and synchronize with the user's intended motion and relay the signal to motors which manage the gears. The robotic suit 230 also protects the user's shoulder, waist, back, and thigh against overload, and stabilizes movements when lifting and holding heavy items.

With continued reference to FIG. 2, secondary detachable robot 240 includes user interface 242 and sensors 244. Secondary detachable robots 240 are collapsible robots that are stored in robotic suit 230. In exemplary embodiments, a secondary detachable robot 240 may include a drone, a legged robot, an autonomous mobile robot, a manually teleoperated robot, a guarded tele-op robot, an autonomously guided robot, a lightweight mobile robot with soft grippers, a controller, sensors, actuators, and a power system, and any other mobile robots known to one of ordinary skill in the art. The sensors used are dependent upon the requirements of the robot, and may include dead reckoning, tactile, and proximity sensing, triangulation ranging, collision avoidance, position location and other specific applications known to one of ordinary skill in the art.

In exemplary embodiments, secondary detachable robot 240 includes user interface 242, which may be a computer program that allows a user to interact with secondary detachable robot 240 and other connected devices via network 202. For example, user interface 242 may be a graphical user interface (GUI). In addition to comprising a computer program, user interface 242 may be connectively coupled to hardware components, such as those depicted in FIG. 1, for sending and receiving data. In an exemplary embodiment, user interface 242 may be a web browser, however in other embodiments user interface 242 may be a different program capable of receiving user interaction and communicating with other devices, such as host server 210.

In exemplary embodiments, user interface 242 may be a touch screen display, a visual display, a remote operated display, or a display that receives input from a physical keyboard or touchpad. In alternative embodiments, user interface 242 may be operated via voice commands or by any other means known to one of ordinary skill in the art.

With continued reference to FIG. 2, sensors 244 can include a device, hardware component, module, or subsystem capable of recording, capturing, and detecting events (e.g., environmental and weather events, etc.) or changes in a user environment, or proximity, and sending the detected data to other electronics (e.g., host server 110), components (e.g., knowledge corpus 252), or programs (e.g., robotic first aid program 220) within a system such as robotic first aid computing environment 200. In various embodiments, the detected data collected by sensors 244 is instrumental in creating a knowledge corpus for first aid treatments.

Sensors 244, in exemplary embodiments, may be a global positioning system (GPS), software application, proximity sensor, camera, microphone, light sensor, infrared sensor, weight sensor, temperature sensor, tactile sensor, motion detector, optical character recognition (OCR) sensor, occupancy sensor, heat sensor, analog sensor (e.g., potentiometers, force-sensing resistors), radar, radio frequency sensor, quick response (QR) code, video camera, digital camera, Internet of Things (IoT) sensors, lasers, gyroscopes, accelerometers, actuators, structured light systems, road condition sensors, traffic sensors, weather sensors, and any other device(s) used for detecting and identifying obstacles or dangerous conditions within a workspace or environment, and for diagnosing injuries and appropriate medical treatments based on the injury.

In exemplary embodiments, sensors 244 are capable of continuously monitoring, collecting, and saving collected data on a local storage, such as knowledge corpus 252, or sending the collected data to robotic first aid program 220. In alternative embodiments, sensors 244 may be capable of detecting, communicating, pairing, or syncing with internet of things (IoT) devices, thus creating opportunities for more direct integration of the physical world into computer-based systems, and resulting in improved efficiency, accuracy, and economic benefit in addition to reduced human intervention.

In exemplary embodiments, database server 250 includes knowledge corpus 252. In various embodiments, database server 250 may be a laptop computer, tablet computer, netbook computer, personal computer (PC), a desktop computer, a personal digital assistant (PDA), a smart phone, a server, or any programmable electronic device capable of communicating with host server 210 and robotic suit 230, via network 202. Database server 250 may include internal and external hardware components, as depicted and described in further detail with reference to FIG. 1. In other embodiments, database server 250 may be implemented in a cloud computing environment, as described in relation to FIG. 1. Database server 250 may also have wireless connectivity capabilities allowing it to communicate with host server 210, robotic suit 230, secondary detachable robot 240, and other computers or servers over network 202.

In exemplary embodiments, knowledge corpus 252 may contain one or more sets of learning data. Learning data may include data sets comprising gathered data from sensors 244, such as first aid treatment data for specific ailments or injuries in various contextual settings, and user settings associated with first aid treatments (e.g., allergies to medication, medical history with specific first aid treatments, etc.).

While knowledge corpus 252 is depicted as being stored on database server 250, in other embodiments, knowledge corpus 252 may be stored on host server 210, robotic first aid program 220, robotic suit 230, secondary detachable robot 240, or any other device or database connected via network 202, as a separate database. In alternative embodiments, knowledge corpus 252 may be comprised of a cluster or plurality of computing devices, working together, or working separately.

With continued reference to FIG. 2, host server 210 includes robotic first aid program 220. Host server 210 may be a laptop computer, tablet computer, netbook computer, personal computer (PC), a desktop computer, a personal digital assistant (PDA), a smart phone, or any programmable electronic device capable of communicating with robotic suit 230 and database server 250, via network 202.

With continued reference to FIG. 2, robotic first aid program 220, in an exemplary embodiment, may be a computer application on host server 210 that contains instruction sets, executable by a processor, for robotically providing first aid treatment to an effected worker, wherein the affected worker is wearing a robotic suit 230 that further comprises an exoskeleton and one or more secondary detachable robots 240.

The instruction sets may be described using a set of functional modules. In exemplary embodiments, robotic first aid program 220 may receive input from robotic suit 230, secondary detachable robot 240, and database server 250, over network 202. In alternative embodiments, robotic first aid program 220 may be a computer application on robotic suit 230, or a standalone program on a separate electronic device.

With continued reference to FIG. 2, the functional modules of robotic first aid program 220 include receiving module 222, identifying module 224, determining module 226, activating module 228, and providing module 229.

Figure 3:
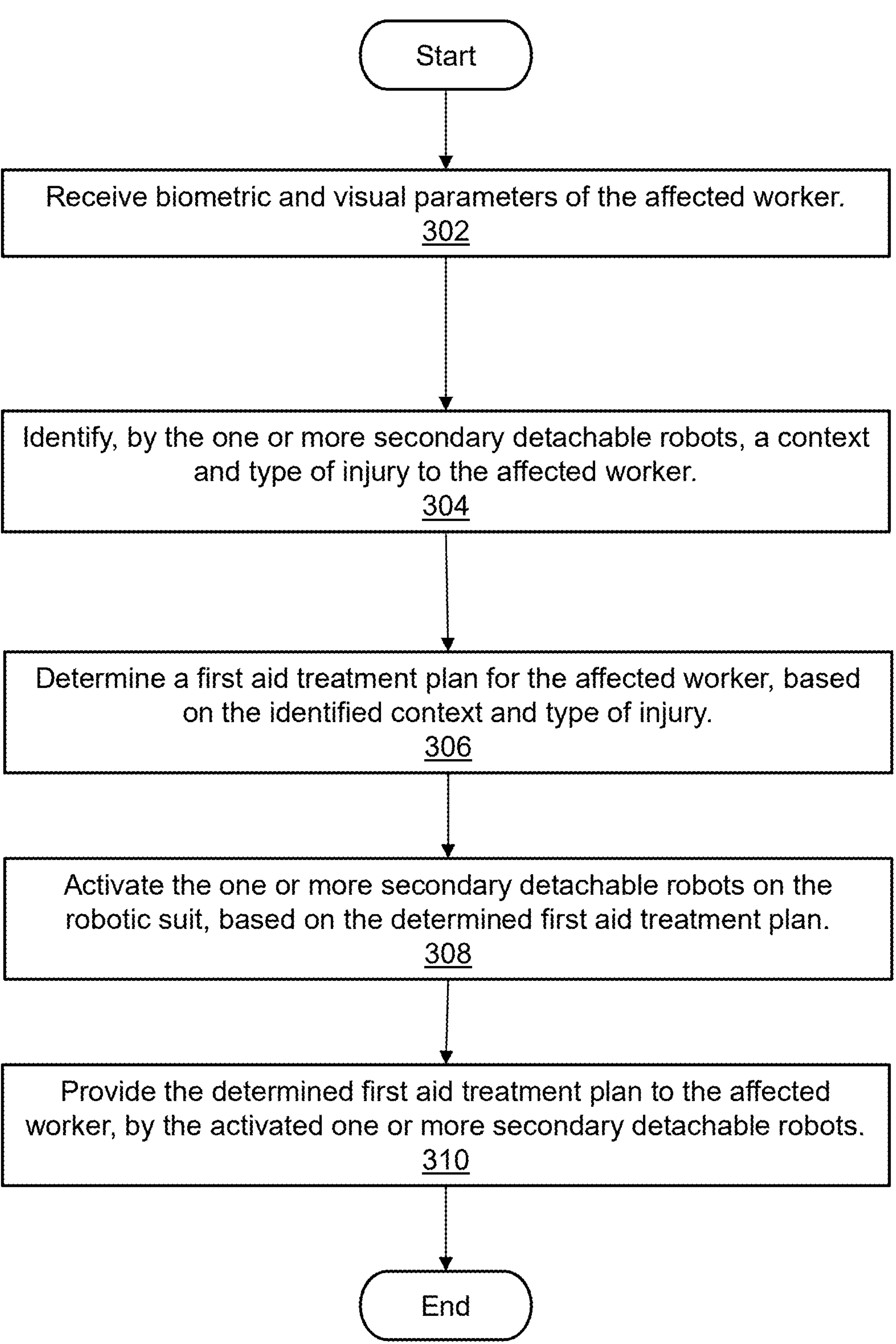
FIG. 3 is a flowchart illustrating the operation of robotic first aid program 220 of FIG. 2, in accordance with an embodiment of the present invention.

FIG. 3 is a flowchart illustrating the operation of robotic first aid program 220 of FIG. 2, in accordance with embodiments of the present disclosure.

With reference to FIGS. 2 and 3, receiving module 222 includes a set of programming instructions, in robotic first aid program 220, to receive biometric and visual parameters of the affected worker (step 302). The set of programming instructions is executable by a processor.

In exemplary embodiments, robotic first aid program 220 includes an opt-in feature, enabling a user to set preferences (e.g., give or revoke permissions) for detecting, monitoring, and identifying a user's medical history, location, individual biometric parameters, and other personal information configured to interact with receiving module 222. A user may opt-out of information sharing with robotic first aid program 220 at any time, at user's discretion.

In exemplary embodiments, biometric parameters may include data relating to the physical, physiological, or behavioral characteristics of an individual. Visual parameters may include the context of a surrounding environment of an individual.

In exemplary embodiments, if a user gets injured on a job site, receiving module 222 receives information with respect to the extent of the injury and whether the job site is safe and free from additional harm that may injure the user (e.g., falling branches, unsteady ground, falling rocks, inclement weather conditions, etc.). Receiving module 222 receives information from sensors 244.

In exemplary embodiments, robotic suit 230 includes one or more secondary detachable robots 240 that are collapsible and stored within chambers of the robotic suit 230. Robotic suit 230 also includes a storage chamber for a first aid kit and additional first aid materials.

In exemplary embodiments, the one or more secondary detachable robots 240 can be attached or detached from the worker's robotic suit 230, based on the context and type of first aid treatment required. For example, the one or more secondary detachable robots 240 will either be detached from the robotic suit 230 or will remain attached to the robotic suit 230 to provide appropriate first aid treatment to the affected worker.

With reference to an illustrative example, Joe is a miner. The mine shaft is only big enough for one miner. Joe operates by himself in the mine shaft and is wearing a robotic suit 230. Joe has suffered a severe laceration on his leg while in the mine shaft. Luckily, his robotic suit 230 is equipped with robotic first aid program 220, which receives medical information (e.g., blood pressure, glucose levels, etc.) together with a context and visual of the surrounding mine shaft where Joe is located. The walls of the mine shaft are determined to be unsturdy and a rescue team is simultaneously alerted to the situation.

With continued reference to FIGS. 2 and 3, identifying module 224 includes a set of programming instructions in robotic first aid program 220, to identify, by the one or more secondary detachable robots, a context and type of injury to the affected worker (step 304). The set of programming instructions is executable by a processor.

In exemplary embodiments, identifying module 224 identifies the type of injury based on gathered information from sensors 444. For example, identifying module 224 identifies a dislocated arm, a torn limb, a laceration, cardiac arrest, and so forth. Further, identifying module 224 identifies the worker's surroundings which might be a threat to the worker and the need to provide an appropriate level of protection until a rescue team arrives to the scene.

In exemplary embodiments, a user authorizes their robotic suit 230 to integrate with robotic first aid program 220.

With continued reference to the illustrative example above, the invention identifies Joe's leg laceration via sensors 244 on the one or more secondary detachable robots 240. Further, Joe is able to communicate with robotic first aid program 220 via user interface 242 to detail his condition and the condition of the surrounding mine shaft.

With continued reference to FIGS. 2 and 3, determining module 226 includes a set of programming instructions in robotic first aid program 220, to determine a first aid treatment plan for the affected worker, based on the identified context and type of injury (step 306). The set of programming instructions is executable by a processor.

In exemplary embodiments, determining module 226 searches a knowledge corpus (i.e., knowledge corpus 252) to determine the first aid treatment plan to be provided to the affected worker based on the identified context and type of injury.

For example, the first aid treatment plan may include stability/support to an affected limb until a rescue team arrives. In other scenarios, time may be of the essence and critical first aid care, or action, must be performed immediately (e.g., cardio-pulmonary resuscitation (CPR), applied pressure to a wound to stop excessive blood loss, moving the affected worker to a safe location to avoid further injury or damage, and so forth).

In exemplary embodiments, determining module 226 weighs the type of injury with the contextual environment to determine a first aid treatment plan.

In further exemplary embodiments, determining module 226 identifies how many of the one or more secondary detachable robots 240 need to be detached from the robotic suit 230 to provide the first aid treatment plan.

In further exemplary embodiments, robotic first aid program 220 detaches, remotely, the one or more secondary detachable robots 240 from the robotic suit 230 to provide the determined first aid treatment plan. For example, the one or more secondary detachable robots 240 may be capable of moving the affected worker and administering the first aid (e.g., performing stitches, etc.).

In alternative embodiments, determining module 226 determines whether the affected worker can perform the first aid treatment plan on their own. If it is determined that the affected worker is not capable of performing the first aid treatment plan on their own, robotic first aid program 220 performs the first aid treatment plan autonomously to the affect worker, via the one or more secondary detachable robots 240.

In further exemplary embodiments, the affected worker may be moved the one or more secondary detachable robots 240 if determining module 226 determines that the surrounding environment is too dangerous. In this scenario, the one or more secondary detachable robots 240 can use GPS technology to meet the arriving rescue team along an identified path away from the dangerous situation. For example, robotic first aid program 220 can communicate with the arriving rescue team to pinpoint an exact location of the arriving rescue team.

With continued reference to the illustrative example above, determining module 226 determines that Joe's severe leg laceration requires applied pressure and stitches. However, determining module 226 also takes into consideration the unsturdy walls of the mine shaft collapsing and causing further damage to Joe. As such, determining modules adjusts the first aid treatment plan to prioritize moving Joe to a safe location while simultaneously applying pressure to his wound. Once Joe is in a safe location, further first aid treatment can be performed.

With continued reference to FIGS. 2 and 3, activating module 228 includes a set of programming instructions in robotic first aid program 220, to activate the one or more secondary detachable robots on the robotic suit, based on the determined first aid treatment plan (step 308). The set of programming instructions is executable by a processor.

In exemplary embodiments, the one or more secondary detachable robots 240 on the robotic suit 230 can remove one or more objects, that pose a risk of further injury, from a surrounding area of the affected worker.

In further exemplary embodiments, activated secondary detachable robots 240 can continue to provide first aid treatment to an affected worker until a rescue team arrives.

In exemplary embodiments, the one or more secondary detachable robots 240 have a flying capability, a walking capability, and one or more robotic arms to provide various types of first aid treatment to the affected worker.

In further exemplary embodiments, the one or more secondary detachable robots 240 are teleoperated, via activating module 228, to provide the determined first aid treatment plan as wells as a real-time visual of the worker's surroundings of the activity area, by a remote second worker.

In alternative embodiments, the teleoperators of the one or more secondary detachable robots 240 can monitor the first aid treatment plan under the supervision and guidance of a remote qualified medical professional with teleoperation or as per the protocol of approved medical councils, until a rescue team arrives. Furthermore, robotic first aid program 220 can notify the affected worker that the rescue team is on their way.

In further exemplary embodiments, the one or more secondary detachable robots 240 remove the appropriate first aid equipment from the robotic suit 230, as determined by the first aid treatment plan, and directed by robotic first aid program 220.

With continued reference to the illustrative example, various secondary detachable robots 240 are activated based on the determined first aid treatment plan for Joe. Initially, a secondary detachable robot 240 removes gauze pads and medical tape from the first aid kit found in Joe's robotic suit 230 and applies pressure to the laceration. Another secondary detachable robot 240 hauls Joe to safe space within the mine shaft until a rescue team arrives on the scene.

With continued reference to FIGS. 2 and 3, providing module 229 includes a set of programming instructions in robotic first aid program 220, to provide the determined first aid treatment plan to the affected worker, by the activated one or more secondary detachable robots (step 310). The set of programming instructions is executable by a processor.

In exemplary embodiments, the secondary detachable robots 240 are coupled with the robotic suit 230, via mechanical or magnetic coupling, and work together to stabilize a position of the injured worker to minimize further injuries.

In alternative embodiments, the secondary detachable robots 240 are trained and programmed in first aid operation and treatment to collaborate with each other.

In exemplary embodiments, prior to commencing any first aid treatment, the secondary detachable robots 240 announce their ability to deliver the determined first aid treatment plan to the affected worker. The worker has the option to accept treatment or deny treatment, either in whole or in part.

With continued reference to the illustrative example, the secondary detachable robots 240 stabilize Joe's laceration and move him to a safe area. While being treated, Joe is in direct communication with a remote qualified medical professional who is monitoring the first aid treatment via teleoperators until the rescue team arrives. Additionally, robotic first aid program 220 keeps Joe updated with the estimated time of arrival for the rescue team.

In exemplary embodiments, network 202 is a communication channel capable of transferring data between connected devices and may be a telecommunications network used to facilitate telephone calls between two or more parties comprising a landline network, a wireless network, a closed network, a satellite network, or any combination thereof. In another embodiment, network 202 may be the Internet, representing a worldwide collection of networks and gateways to support communications between devices connected to the Internet. In this other embodiment, network 202 may include, for example, wired, wireless, or fiber optic connections which may be implemented as an intranet network, a local area network (LAN), a wide area network (WAN), or any combination thereof. In further embodiments, network 202 may be a Bluetooth network, a WiFi network, or a combination thereof. In general, network 202 can be any combination of connections and protocols that will support communications between host server 210, robotic suit 230, and database server 250.

The invention claimed is:

1. A computer-implemented method for robotically providing first aid treatment to an affected worker, wherein the affected worker is wearing a robotic suit that further comprises an exoskeleton and one or more detachable secondary robots, and wherein the one or more detachable secondary robots are coupled with the robotic suit via magnetic coupling, and wherein the one or more secondary robots are stored within chambers of the robotic suit, the computer-implemented method comprising:

receiving biometric and visual parameters of the affected worker;

identifying, by the one or more secondary detachable robots, a context and type of injury to the affected worker;

determining a first aid treatment plan for the affected worker, based on the identified context and type of injury;

activating the one or more secondary detachable robots on the robotic suit, based on the determined first aid treatment plan, wherein each of the one or more secondary detachable robots provide various types of first aid treatment to the affected worker; and providing, autonomously, the determined first aid treatment plan to the affected worker, by the activated one or more secondary detachable robots, as well as a real-time visual of the affected worker's surrounding of an activity area;

based on detecting and identifying obstacles or dangerous conditions within the affected worker's surrounding of the activity area, moving the affected worker to a safe location;

coordinating the one or more secondary detachable robots, via global positioning system (GPS), to meet an arriving rescue team along an identified path away from the detected obstacles or dangerous conditions; and continuing to provide first aid treatment to the affected worker until handoff to the arriving rescue team.

2. The computer-implemented method of claim 1, wherein the one or more secondary detachable robots are teleoperated to provide the determined first aid treatment plan by a remote second worker.

3. The computer-implemented method of claim 2, further comprising:

monitoring, by the teleoperators, the first aid treatment plan under the supervision and guidance from a remote qualified medical professional until a rescue team arrives; and notifying the affected worker that the rescue team is on their way.

4. The computer-implemented method of claim 1, wherein the one or more secondary detachable robots have a flying capability, a walking capability, and one or more robotic arms to provide various types of first aid treatment to the affected worker.

5. The computer-implemented method of claim 1, further comprising:

removing one or more objects, that pose a risk of further injury, from a surrounding area of the affected worker; and providing continued first aid treatment to the affected worker until a rescue team arrives.

6. The computer-implemented method of claim 1, further comprising:

determining whether the affected worker is capable of performing the first aid treatment plan on their own; and performing the first aid treatment plan autonomously to the affected worker, if it is determined that the affected worker is not capable of performing the first aid treatment plan on their own.

7. The computer-implemented method of claim 1, further comprising:

searching a knowledge corpus to determine the first aid treatment plan to be provided to the affected worker based on the identified context and type of injury;

identifying how many of the one or more secondary detachable robots need to be detached from the robotic suit to provide the first aid treatment plan; and detaching, remotely, the one or more secondary detachable robots from the robotic suit to provide the determined first aid treatment plan.

8. A computer program product, comprising a non-transitory tangible storage device having program code embodied therewith, the program code executable by a processor of a computer to perform a method for robotically providing first aid treatment to an affected worker, wherein the affected worker is wearing a robotic suit that further comprises an exoskeleton and one or more detachable secondary robots, and wherein the one or more detachable secondary robots are coupled with the robotic suit via magnetic coupling, and wherein the one or more secondary robots are stored within chambers of the robotic suit, the method comprising:

receiving biometric and visual parameters of the affected worker;

identifying, by the one or more secondary detachable robots, a context and type of injury to the affected worker;

determining a first aid treatment plan for the affected worker, based on the identified context and type of injury;

activating the one or more secondary detachable robots on the robotic suit, based on the determined first aid treatment plan, wherein each of the one or more secondary detachable robots provide various types of first aid treatment to the affected worker; and providing, autonomously, the determined first aid treatment plan to the affected worker, by the activated one or more secondary detachable robots, as well as a real-time visual of the affected worker's surrounding of an activity area;

based on detecting and identifying obstacles or dangerous conditions within the affected worker's surrounding of the activity area, moving the affected worker to a safe location;

coordinating the one or more secondary detachable robots, via global positioning system (GPS), to meet an arriving rescue team along an identified path away from the detected obstacles or dangerous conditions; and continuing to provide first aid treatment to the affected worker until handoff to the arriving rescue team.

9. The computer program product of claim 8, wherein the one or more secondary detachable robots are teleoperated to provide the determined first aid treatment plan by a remote second worker.

10. The computer program product of claim 9, further comprising:

monitoring, by the teleoperators, the first aid treatment plan under the supervision and guidance from a remote qualified medical professional until a rescue team arrives; and notifying the affected worker that the rescue team is on their way.

11. The computer program product of claim 8, wherein the one or more secondary detachable robots have a flying capability, a walking capability, and one or more robotic arms to provide various types of first aid treatment to the affected worker.

12. The computer program product of claim 8, further comprising:

removing one or more objects, that pose a risk of further injury, from a surrounding area of the affected worker; and providing continued first aid treatment to the affected worker until a rescue team arrives.

13. The computer program product of claim 8, further comprising:

determining whether the affected worker is capable of performing the first aid treatment plan on their own; and performing the first aid treatment plan autonomously to the affected worker, if it is determined that the affected worker is not capable of performing the first aid treatment plan on their own.

14. The computer program product of claim 8, further comprising:

searching a knowledge corpus to determine the first aid treatment plan to be provided to the affected worker based on the identified context and type of injury;

identifying how many of the one or more secondary detachable robots need to be detached from the robotic suit to provide the first aid treatment plan; and detaching, remotely, the one or more secondary detachable robots from the robotic suit to provide the determined first aid treatment plan.

15. A computer system, comprising one or more computer devices each having one or more processors and one or more tangible storage devices; and a program embodied on at least one of the one or more storage devices, the program having a plurality of program instructions for execution by the one or more processors, the program instructions comprising instructions for robotically providing first aid treatment to an affected worker, wherein the affected worker is wearing a robotic suit that further comprises an exoskeleton and one or more detachable secondary robots, and wherein the one or more detachable secondary robots are coupled with the robotic suit via magnetic coupling, and wherein the one or more secondary robots are stored within chambers of the robotic suit, the plurality of program instructions further comprise instructions for:

receiving biometric and visual parameters of the affected worker;

identifying, by the one or more secondary detachable robots, a context and type of injury to the affected worker;

determining a first aid treatment plan for the affected worker, based on the identified context and type of injury;

activating the one or more secondary detachable robots on the robotic suit, based on the determined first aid treatment plan, wherein each of the one or more secondary detachable robots provide various types of first aid treatment to the affected worker; and providing, autonomously, the determined first aid treatment plan to the affected worker, by the activated one or more secondary detachable robots, as well as a real-time visual of the affected worker's surrounding of an activity area;

based on detecting and identifying obstacles or dangerous conditions within the affected worker's surrounding of the activity area, moving the affected worker to a safe location;

coordinating the one or more secondary detachable robots, via global positioning system (GPS), to meet an arriving rescue team along an identified path away from the detected obstacles or dangerous conditions; and continuing to provide first aid treatment to the affected worker until handoff to the arriving rescue team.

16. The computer system of claim 15, wherein the one or more secondary detachable robots are teleoperated to provide the determined first aid treatment plan by a remote second worker.

17. The computer system of claim 16, further comprising:

monitoring, by the teleoperators, the first aid treatment plan under the supervision and guidance from a remote qualified medical professional until a rescue team arrives; and notifying the affected worker that the rescue team is on their way.

18. The computer system of claim 15, wherein the one or more secondary detachable robots have a flying capability, a walking capability, and one or more robotic arms to provide various types of first aid treatment to the affected worker.

19. The computer system of claim 15, further comprising:

removing one or more objects, that pose a risk of further injury, from a surrounding area of the affected worker; and providing continued first aid treatment to the affected worker until a rescue team arrives.

20. The computer system of claim 15, further comprising:

determining whether the affected worker is capable of performing the first aid treatment plan on their own; and performing the first aid treatment plan autonomously to the affected worker, if it is determined that the affected worker is not capable of performing the first aid treatment plan on their own.

* * * * *